United States Patent [19]

Turley

[11] 4,218,405

[45] Aug. 19, 1980

[54] HALOGENATED TERTIARY PHOSPHITE ESTERS

[75] Inventor: Richard J. Turley, Orange, Conn.

[73] Assignee: Olin Corporation, New Haven, Conn.

[21] Appl. No.: 899,919

[22] Filed: Apr. 26, 1978

[51] Int. Cl.² .......................... C07F 9/141; C08K 5/53
[52] U.S. Cl. ........................... 260/967; 260/45.7 PH; 252/188.3 R
[58] Field of Search ........................................ 260/967

[56] References Cited

U.S. PATENT DOCUMENTS

| | | | |
|---|---|---|---|
| 2,169,185 | 8/1939 | Shoemaker et al. | 260/967 X |
| 3,184,495 | 5/1965 | Barnauckas et al. | 260/967 X |
| 3,318,978 | 5/1967 | Palethorpe | 260/928 OR |
| 3,399,217 | 8/1968 | Zaslowsky | 260/348.6 |
| 3,553,298 | 1/1971 | Hodan et al. | 260/967 OR |
| 3,796,821 | 12/1972 | Anderson et al. | 260/967 X |
| 3,810,961 | 5/1974 | Pivawer | 260/977 |
| 3,883,620 | 5/1975 | Turley | 260/963 OR |
| 3,923,844 | 12/1975 | Pivawer | 260/348.6 |

OTHER PUBLICATIONS

Noller, "Chemistry of Organic Compounds," (1966), 3rd Edition, p318.

*Primary Examiner*—Anton H. Sutto
*Attorney, Agent, or Firm*—F. A. Iskander

[57] ABSTRACT

Disclosed are novel halogenated tertiary phosphite esters which are the reaction product of 4,4,4-trichloro-1,2-epoxybutane or 2,4,4,4-tetrachlorobutanol with a phosphorus trihalide. These compounds are useful as flame retardant additives in plastic resin compositions.

2 Claims, No Drawings

HALOGENATED TERTIARY PHOSPHITE ESTERS

Current and anticipated regulations restricting the flammability of plastic wares has required the manufacturers of plastic articles to implement effective ways to fire retard these materials. Such efforts have produced a variety of fire retardant compounds which can be incorporated into the resin mixtures. Phosphorus and halogen addition compounds, in particular, have been found to impart favorable fire-retardancy properties.

Novel halogenated phosphite esters have now been developed, according to the present invention, which are useful as fire retardant additives for various plastic compositions. These chlorinated alkyl tertiary phosphites offer a favorable balance of cost, fire retardance, and useful resin property modification.

The novel compounds of the present invention are addition products of 4,4,4-trichloro-1,2-epoxybutane and 2,4,4,4-tetrachlorobutanol with a phosphorus trihalide.

The compound 2,4,4,4-tetrachlorobutanol (TCBA) is a well-known versatile compound with a wide range of utilities. It can be prepared by various conventional methods. For example, U.S. Pat. No. 3,399,217 describes a method for preparation of TCBA by the catalyzed reaction of carbon tetrachloride and allyl alcohol. TCBA reacts in a manner typical of aliphatic alcohols, and, in addition, may be readily dehydrohalogenated to yield the compound 4,4,4-trichloro-1,2-epoxybutane (TCBO). TCBO is a well-known reactive, high chlorine-containing epoxide useful in the preparation of epoxy resins, lubricants, polyurethane foams, and the like. An exemplary method for production of TCBO by dehydrohalogenation of TCBA is described in U.S. Pat. No. 3,923,844.

The chlorinated tertiary phosphites of the present invention can readily be prepared by methods known in the art involving reaction of a phosphorus trihalide with an alkylene oxide or an alcohol (e.g., see U.S. Patent No. 3,810,961 and Noller, *Chemistry of Inorganic Compounds*, Third Edition (1966) page 318). Any suitable molar ratio of phosphorus trihalide to TCBO or TCBA can be employed; however, it is preferred to use stoichiometric proportions of reactants, i.e., about three moles of TCBO or TCBA per each mole of phosphorus trihalide. More in detail, the reactions by which the present compounds can be made are represented by Equations I and II as follows:

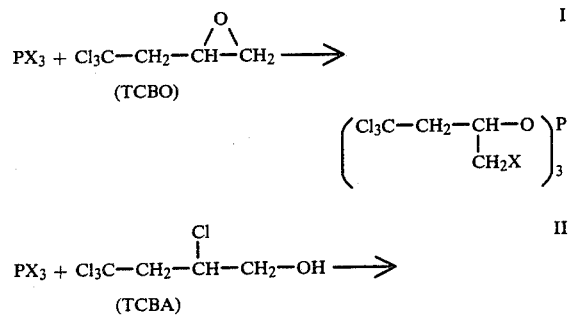

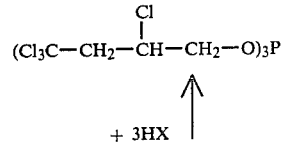

in which X is a halogen.

In carrying out these reactions, it is contemplated that any phosphorus trihalide may be employed; i.e., X can be chlorine, bromine, iodine or fluorine. However, it is preferred to employ those phosphorus trihalides in which the halogen is chlorine, bromine, or mixtures thereof. Phosphorus trichloride is particularly preferred.

In addition to all TCBO or TCBA phosphite esters, derived from reaction of three moles of TCBA or TCBO per mole of phosphorus trihalide, novel tertiary phosphite esters, according to the present invention, having one or more other constituents can also be readily prepared. These compounds are represented by the formula:

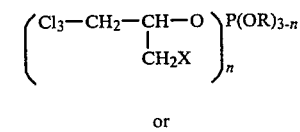

or

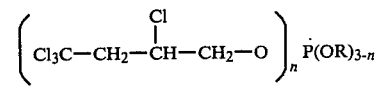

wherein X is a halogen; n is an integer from one to three; and, each R radical is independently selected from alkyl of 1 to about 20 carbon atoms, 2-haloalkyl of about two to about eight carbon atoms, alkaryl, aryl, halogenated aryl, and arylalkyl.

These compounds are prepared by employing reactant combinations of TCBO and TCBA, as well as combinations of other alkylene oxides, alcohols, and phenols with the TCBO and TCBA. At least one or more moles of TCBO or TCBA per mole of phosphorus trihalide is used, with the remaining one or two moles of reactant replaced with other alcohols, phenols and/or epoxides. Accordingly, aliphatic alcohols (with or without heteroatoms, such as sulfur, phosphorus, and oxygen) up to about 20 carbon atoms can be used. These typically include methanol, ethanol, butanol, isopropanol, isobutanol, 2-methoxyethanol, TCBA, other halogenated alcohols, and the like. Supplemental epoxides that can be used are alkylene oxides having a 1,2-epoxide ring. Illustrative are ethylene oxide, propylene oxide, butylene oxide, pentylene oxide, epichlorohydrin, trichloropropylene oxide, trichlorobutylene oxide, TCBO, hexylene oxide, octylene oxide, and the like. Usually, these oxides contain from two to eight, and most preferably from two to four carbon atoms. Further, phosphites containing alkaryl substituents can be prepared by including alkyl phenol reactants such as p-tert-butylphenol, nonyl phenol, 1,2,3 trimethyl phenol, 1,2 diethyl phenol, and other derivatives of phenol, naphthol, cresol, BHT, and the like. Halogenated aryl phosphite ester substituents can be accomplished through use of halogenated phenol reactants such as trihalo-phenol derivatives. Arylalkyl substituents can be made from reaction with arylalkyl alcohols such as benzyl alcohol, 2-phenyl ethanol, and other such substituted alcohols of up to about 20 carbon atoms.

To catalyze the reaction of TCBO and TCBA, and other epoxide and alcohol reactants, with the phosphorus trihalide, tertiary amines, such as pyridine, tributylamine, triethylamine, N,N-dimethylaniline, picoline, lutidine, and the like, can be used. The use of pyridine is preferred. The amine not only serves to catalyze the reaction but also serves as a scavenger for the by-product hydrohalic acid whose presence might otherwise initiate decomposition. In the preparation of phosphite esters from phosphorus trihalide and an alcohol, absence of the amine catalyst usually results in cleavage of the phosphite by the hydrogen halide generated to produce dialkyl phosphites, phosphonates, and other undesirable side products. It has surprisingly been discovered that in the reaction of TCBA and phosphorus trihalide, and amine HCl scavenger is not required in order to preserve the integrity of the tertiary phosphite.

Although the reaction may be run in the absence of a solvent, it is generally preferred to employ a convenient solvent medium. Any inert organic liquid which is a solvent for both the catalyst and the phosphorus trihalide may be employed for this purpose, such as ethylene dichloride.

The novel tertiary phosphite esters of the present invention are particularly useful as fire retardant additives for epoxy resins.

Various epoxy resins have been known in the prior art. Widely used such resins include the glycidyl ethers which are prepared, for example, by reacting an epihalohydrin with hydroxylated compounds. In the presence of a catalyst, these resins cure into solid materials that are commonly used in the manufacture of coatings, molding compositions and adhesives.

In general, it is also known that the burning properties of epoxy resins can be modified or reduced by the incorporation of chlorine therein. According to the prior art, this may be achieved by the addition of a non-reactive, chlorine-containing material, e.g., chlorinated phenol and dichlorohydrin, such a material being usually combined with antimony oxide to enhance the effect of the chlorine in reducing the combustibility of the resin. See also Russian Pat. No. 191,021 which discloses the incorporation of chlorinated polyethylene in epoxy adhesives. Alternatively, the chlorine may be chemically bound to the resin as taught in U.S. Pat. Nos. 2,839,496 and 3,496,120. The former patent teaches the use of 1,4,5,6,7,7-hexachloro-2-(2,3-epoxypropoxymethyl)-bicyclo(2,2,1)hept-5-ene as a reactive diluent with epoxide condensation products. And U.S. Patent No. 3,496,120 discloses the preparation of polyether epoxide compositions by reacting together an epihalohydrin, a polyol, and a chlorinated alkylene oxide such as 4,4,4-trichloro-1,2-epoxybutane. The polyepoxide products of such a reaction are then dehydrohalogenated to yield resinous materials which can be cross-linked into hard plastics that are said to be non-burning.

Any of the variety of prior art liquid, curable epoxy resins having more than one α-epoxy group in the molecule may be used in the composition of the invention. However, it is generally preferred to employ the glycidyl ether type epoxy resins. These are generally prepared by reacting an epihalohydrin with a polyhydroxy compound in a liquid caustic medium. Such and other epoxy resins and their preparation are described in detail in H. Lee and K. Neville, *Handbook of Epoxy Resins*, McGraw-Hill, Inc., New York (1967). The entire disclosure of this book is incorporated herein by reference.

Illustrative glycidyl type epoxy resins include the glycidyl ethers of bisphenols such as bisphenol-A, the glycidyl ethers of mononuclear di- and trihydric phenols, the glycidyl ethers of aliphatic polyols, the glycidyl ethers of novolac resins, and the glycidyl ethers of polynuclear phenols. Because of their ready commercial availability, the glycidyl ethers of bisphenol-A, are especially preferred such as may be represented by the structural formula:

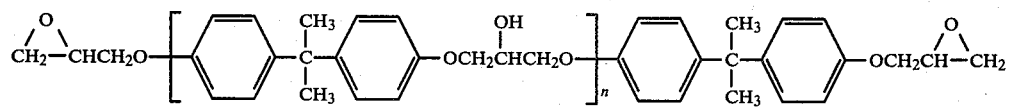

wherein n represents a number of one or less.

The epoxy resin composition of the invention includes a curing agent or catalyst. Here again any such material known in the prior art to be an effective curing agent for a particular epoxy resin as defined herein or for any generic group of epoxy resins may be employed where feasible or desirable. This may include two or more ingredients which act together as a curing system for the epoxy resin. The curing agent or system, when mixed with the epoxy resin, serves to transform it from the liquid or thermoplastic state to a hard thermoset solid; and, depending on the nature of the particular curing agent, this transformation occurs by the curing agent acting as a catalyst to promote the curing process, or the curing agent may participate in a reaction with the epoxy resin thereby becoming chemically bound into the resin chain.

Illustrative epoxy resin curing agents include basic materials, such as the Lewis bases, the inorganic bases, the primary and secondary amines, and the amides; and acidic materials such as the Lewis acids, the carboxylic acid anhydrides, and the dibasic organic acids. These and other curing agents are described in detail in the above-cited *Handbook of Epoxy Resins*.

The curing agent is employed in any suitable proportion which is effective in curing the epoxy resin. As is well known in the art, such proportion depends largely on the chemical nature of the curing agent and on the rate of curing which is desired. Therefore, a specific proportion which is applicable in the case of one curing agent may represent an insufficient or excessive level, as the case may be, when a different curing agent is used. Thus, the term "effective amount", as used in the specification and claims herein with reference to the curing agent, is intended to encompass any such proportion of a particular curing agent or group of curing agents which may suitably be used to bring about curing of the epoxy resin. For general illustration, depending on the particular material used, the curing agent may be employed in a proportion of about 4–100 parts per every 100 parts by weight of the epoxy resin.

In addition to the curing agent, if desired, other ingredients may be added to the epoxy resin, such as taught in the prior art, in order to modify the properties of the resin or to achieve certain objectives in connection with its processing and commercial utilization. This includes, for example, fillers, solvents or diluents, resin modifiers, and plasticizers.

Pursuant to the invention, reduced combustibility is imparted to the epoxy resin by incorporating or mixing therewith the novel tertiary phosphite esters as defined above.

The tertiary phosphite additive may be used in any proportion which is effective in reducing the combustibility of the epoxy resin. For example, such a proportion may be obtained by blending the epoxy resin with about 1 to about 80 percent by weight, preferably about 1 to about 70 percent by weight of the tertiary phosphite additive. The most preferred range is about 10 to about 40 percent by weight of the tertiary phosphite additive.

In preparing the epoxy composition of the invention, the tertiary phosphite additive and the curing agent are simply added to, and mixed with, the epoxy resin along with any other additives or diluents that may desirably be used. Thereafter, the mixture is allowed to cure into a hard substance. Ordinarily, such curing will take place at room temperature, so that elevated temperatures are not necessary. However, in practive, it is preferred to employ moderately elevated temperatures, such as about 30°–100° C., and more preferably about 40°–80° C., in order to speed up the curing process.

Upon curing, the epoxy composition of the invention exhibits marked reduction in combustibility. As such, it can be used to advantage in various coating, potting, casting and molding applications in which varying degrees of resistance to burning are required.

The tertiary phosphite esters of the present invention also are effective as fire retardant additives for polyvinylchloride (PVC), and polyurethane resins. These phosphite esters further are useful as plasticizers and resin stabilizers. The high chlorine content of these phosphites results in good organic solubility, decreased water solubility, and good effectiveness in fire retardance. The products are also useful as functional fluids and lubricant additives.

The following examples are provided to further illustrate the invention. All parts and percentages given are by weight, unless otherwise specified. Temperatures given are degrees centigrade.

EXAMPLE I

Preparation of Tris-(1,4,4,4-Tetrachloro-2-Butyl) Phosphite

About 1 ml each TCBA (2,4,4,4-tetrachlorobutanol) and pyridine were added to 0.4 mole phosphorus trichloride in 100 ml methylene chloride. A total of 1.2 moles TCBO (4,4,4-trichlorobutylene-1,2 oxide) was then added to the well-stirred solution at 20°–30° in about two hours. The reaction mixture was stirred at room temperature for about one hour after the addition was completed. Most of the solvent was then removed by warming under reduced pressure. A total of 2 ml triethylamine was added to neutralize residual acidity. The product was then heated to 60° at 1 mm for about one hour to remove residual volatiles. The nature of the phosphite product, obtained in 100% yield, was confirmed by infrared and nuclear magnetic resonance analyses.

Calcd. for $C_{12}H_{15}Cl_{12}O_3P$: %Cl, 64.16; %P, 4.67. Found: %Cl, 63.88; %P, 4.80.

In a separate reaction, the addition of TCBO to phosphorus trichloride in methylene chloride without pyridine resulted in a very mildly exothermic reaction. Subsequent work-up yielded a product with considerably greater viscosity than expected. This reaction apparently resulted in the formation of a TCBO-polymer.

EXAMPLE II

Preparation of Bis-(1,4,4,4-Tetrachloro-2-Butyl) Butyl Phosphite

A total of 1.2 moles TCBO was added dropwise to a solution of 0.6 mole phosphorus trichloride in 250 ml carbon tetrachloride and 200 ml methylene chloride containing about 1 ml each TCBA and pyridine. The temperature of the exothermic reaction was kept at 45°–52°. After the reaction was completed, another 150 ml carbon tetrachloride was added. A mixture of 0.6 mole butanol and 0.6 mole pyridine was then added to the well-stirred solution at 15°–20°. After the reaction mixture was stirred for 20 minutes at room temperature, the mixture was filtered free of salts. The solvent was removed by warming under reduced pressure. Residual volatiles were removed by heating to 50° at 2 mm for about one hour. The phosphite product, obtained in 96% yield, was treated with 2 ml triethylamine to neutralize residual acidity. The nature of the product was confirmed by infrared spectroscopy; n(27/D) 1.5053.

Calcd. for $C_{12}H_{19}Cl_8O_3P$: %Cl, 53.99; %P, 5.89. Found: %Cl, 53.79; %P, 5.60.

EXAMPLE III

Preparation of Bis-(1,4,4,4-Tetrachloro-2-Butyl) p-Tert-Butylphenyl Phosphite

A total of 0.5 mole p-tert-butylphenol was added portionwise to a well-stirred solution of 0.5 mole phosphorus trichloride in 100 ml carbon tetrachloride at room temperature. The mixture was stirred for 1.5 hours at room temperature after the addition was completed. The residual HCl by-product was expelled by heating the solution to 79°. After about 1 ml pyridine and 50 ml methylene chloride was added at about 50°, the TCBO was added dropwise at 57°–62° over a two-hour period. The reaction mixture was then stored for about 18 hours at room temperature. Subsequent work-up was carried out as described above, the neutralized product was clarified by filtration, to give 84% yield of product, n(26/D) 1.5341.

EXAMPLE IV

Preparation of Tris-(2,4,4,4-Tetrachlorobutyl) Phosphite

A total of one mole TCBA was added dropwise to well-stirred 0.5 mole phosphorus trichloride in the absence of solvent. The temperature of the reaction was kept at or below room temperature by the escaping HCl gas. An additional 0.5 mole TCBA was then added under reduced pressure to assist the removal of HCl. After the addition was completed, the reaction mixture was stirred for two hours under reduced pressure. Residual acidity in the product was neutralized by the addition of 1 ml triethylamine. The product, obtained in 95% yield, was clarified by filtration: n(25/D) 1.5237. Analysis by nuclear magnetic resonance spectroscopy showed the product was at least 93% tertiary phosphite.

Calcd. for $C_{12}H_{15}Cl_{12}O_3P$: %Cl, 64.16; %P, 4.67. Found: %Cl, 64.42; %P, 4.59.

EXAMPLE V

Preparation of Bis-(2,4,4,4-Tetrachlorobutyl) Butyl Phosphite

A total of 1.2 moles TCBA was added dropwise to a well-stirred solution of 0.6 mole phosphorus trichloride in 100 ml carbon tetrachloride. The escaping HCl caused the reaction temperature to drop from 20° to 18°. After the addition was completed, the solution was stirred at room temperature for 0.5 hour. Most of the solvent and entrained HCl was removed by heating the solution to 50° at about 2 mm pressure. The residual product was redissolved in 300 ml carbon tetrachloride and was then treated dropwise with a mixture of 0.6 mole butanol and 0.9 mole pyridine. After the mixture was post-reacted for 0.5 hour at room temperature, the solution was filtered free of salts. The solvent and other volatiles were removed by warming under reduced pressure to give a 95% yield of product, which was further clarified by filtration with the aid of Celite: n(27/D) 1.5058. The nature of the product as a tertiary phosphite was demonstrated by infrared spectroscopy.

Calcd. for $C_{12}H_{19}Cl_8O_3P$: %Cl, 53.99; %P, 5.89. Found: %Cl, 54.27; %P, 5.42.

EXAMPLE VI

Preparation of Bis-(2,4,4,4-Tetrachlorobutyl) p-Tert-Butylphenyl Phosphite

The solid phenol (0.5 mole) was added portionwise to phosphorus trichloride (0.5 mole) in 100 ml methylene chloride with good stirring at room temperature. After a post-reaction for about two hours at room temperature, the solution was refluxed for 45 minutes. A total of one mole TCBA was then added dropwise with good stirring at room temperature. The escaping HCl by-product lowered the reaction temperature so that external cooling was not required. After a 20-minute stirring at room temperature, the solution was stirred under reduced pressure at about 50° for about one hour. A final strip of volatiles at 2 mm pressure gave 100% yield of colorless product. Residual acidity was neutralized with 4 ml triethylamine; n(27/D) 1.5310. The nature of the product was substantiated by infrared analysis.

Calcd. for $C_{18}H_{23}Cl_8O_3P$: %Cl, 47.18; %P, 5.15. Found: %Cl, 47.47, %P, 5.02.

EXAMPLES VII-VIII

Epoxy Resin Preparation

The phosphite additive was blended with a mixture of diglycidyl ether of bisphenol-A (DGEBA, obtained from Shell Chemical Co. as Epon 828) and an amine curing agent (TETA, triethylene tetraamine) in various proportions. The premixed epoxy resin and curing agent consisted of 12 g curing agent per 100 g resin. The phosphite-resin mixture was poured into an aluminum cup and was allowed to cure for seven days at room temperature. The mixture may be cured faster at elevated temperature. The products thus formed were hard glossy substances which often proved to be difficult to ignite by flame. None of the castings showed any "bleeding" of the additive on the surface. Test results of these epoxy compositions are reported in Table A, below.

TABLE A

| EXAMPLE VII | | | | | | |
|---|---|---|---|---|---|---|
| Phosphite Compound 1 (wt. %) | 0 | 10 | 20 | 30 | 40 | 50 |
| Shore D | 85 | 83 | 86 | 81 | 68 | 60 |
| Flammability | B | B | SE | SE | SE/DNI | DNI |
| EXAMPLE VIII | | | | | | |
| Phosphite Compound 2 (wt. %) | | 10 | | 30 | | 50 |
| Shore D | | 86 | | 80 | | 68 |
| Flammability | | B | | SE | | DNI |

1: tris-(2,4,4,4-tetrachlorobutyl) phosphite, the reaction product of TCBA and $PCl_3$.
2: tris-(1,4,4,4-tetrachloro-2-butyl) phosphite, the reaction product of TCBO and $PCl_3$.
B: sample readily ignited by a flame and continued to burn when the flame source was removed.
SE: sample ignited with some difficulty and did not sustain a flame when the ignition source was removed.
DNI: sample did not ignite during the application of a flame.

I claim:
1. The compound identified as tris-(1,4,4,4-tetrachloro-2-butyl) phosphite.
2. The compound identified as tris-(2,4,4,4-tetrachlorobutyl) phosphite.

* * * * *